US00PP10480P

United States Patent [19]

Nadori

[11] Patent Number: Plant 10,480

[45] Date of Patent: Jul. 7, 1998

[54] MANDARIN TANGERINE CALLED NADORCOTT

[75] Inventor: El Bachir Nadori, Agdal-Rabat, Morocco

[73] Assignee: Jean de Maistre, Porticragnos, France

[21] Appl. No.: 787,028

[22] Filed: Jan. 28, 1997

[51] Int. Cl.[6] ..... A01H 5/00

[52] U.S. Cl. ..... Plt./45

[58] Field of Search ..... Plt./45

*Primary Examiner*—James R. Feyrer

*Attorney, Agent, or Firm*—Townsend and Townsend and Crew

[57] ABSTRACT

A new variety of Mandarin Tangerine called 'Nadorcott' is distinguished by its seedless fruit under self-pollination conditions. The fruit is easy peeling with a superior rind and juice color when compared to 'Murcott.' The fruit has excellent aroma and flavor, ease of segment separation, tender segment skin and is mid-season maturing with a highly productive yield even for young trees.

5 Drawing Sheets

DESCRIPTION

Field of the Invention

This application is being filed pursuant to the provisions of the International Union for the Protection of New Varieties of Plants (U.P.O.V.).

This invention comprises a novel variety of Mandarin Tangerine tree (*Citrus reticulata* Blanco) presently named 'Nadorcott' which is primarily characterized by its seedless and easy peeling fruit and by its attractive orange red rind color.

BACKGROUND AND ASEXUAL REPRODUCTION OF THE NEW VARIETY

In 1982, the inventor observed a variety of Mandarin among 18 year old 'Murcott' trees planted in 1964 in a nucellar selection program plot in INRA experiment station near Afourer town. The selection, assigned experimental code 'Inra W,' is believed to be the result of a chance cross-pollination between the 'Murcott' Mandarin as a seed bearing parent and an unknown pollen parent.

Budwood of 'Inra W' was asexually propagated on a small scale for experimental purposes at the Sasma Nursery in Menasra at the region of Kenitra. Later and in early 1983, experimental plots of 2 to 4 hectares were also established at Kedima and Mokala near Taroudant in the Souss Valley, southwest of Morocco and also in a plot near Marrakech City. In 1985, the young trees bore fruit of the same characteristics as those produced by the original tree, namely, fruit with a superior rind color which was orange red as distinguished from the yellowish orange of the 'Murcott' fruit. However, 'Inra W' was rejected as a commercial variety because of its high seed content.

In the spring of 1988, the inventor observed five-year old trees of 'Inra W' planted under the 'Murcott Sasma' name on a farm belonging to the Domaines Agricoles Company in Rabat. Those trees were renamed 'Afourer' and the inventor noticed that while some yellowish green fruits of these trees, which resulted from out of season blooming, were seedless, the red orange fruits were very seedy. This is the discovery of the present invention. Experiments were conducted to better understand the seedless phenomenon. Accordingly, two five-year old trees of 'Afourer' were covered by an insect proof screen before the next flowering period. The covered trees produced complete seedless fruit while all the fruit produced by the non-covered trees were highly seedy.

In 1990–1991, an experimental orchard was established in a location remote from other citrus trees 30 kilometers from Marrakech City where no citrus was located. At this orchard, it was verified that the new variety is seedless only if cross-pollination is prevented. An average of only 0.2 to 0.5 seed per fruit was found in a sample of 3,000 fruits.

The trees of the orchard near Marrakech were asexually reproduced by grafting budwood onto sour orange rootstock. The result was a variety which is highly homogenous, genetically stable and highly reproductive at an early age. For example, 15 metric tons of fruit per hectare at three years after planting and 30 metric tons of fruit per hectare after four years of planting were produced.

The new variety, called 'Nadorcott', matures by mid-December and harvest starts in January and ends by late March.

Two other experimental orchards were established in 1991 and 1992 in Beni Mellal and also in the area north of Rabat. The orchard at Beni Mellal was discarded because its distance from other citrus groves was insufficient to prevent cross-pollination from other citrus varieties. The experimental farm north of Rabat has been maintained.

Two rootstock trials were carried out in the Taroudant and Marrakech areas in 1992 and 1993. The trials included the rootstock of 'Sour Orange,' 'Cleopatra Mandarin,' 'Troyer Citrange,' 'Citrus Volkameriana,' 'Rangpur Lime,' 'Rough Lemon,' 'Orlando Tangelo' and 'Citrumelo Sacaton.' Preliminary results indicate that the essential characteristics of 'Nadorcott' are not affected by the listed rootstocks. When budded on 'Troyer Citrange,' there was no abnormality or bud union crease.

Studies of hand cross-pollination were made between 'Nadorcott', and other seedy and seedless varieties. For each combination, 'Nadorcott' was used as a female parent and as a pollinator. The studies show that when self-pollinated, 'Nadorcott' is seedless while the parent variety, 'Murcott,' is seedy. The average number of seeds per fruit when 'Nadorcott' was used as a pollinator or as a seed bearing parent ranged from 5 to 35 depending on the combination.

DETAILED DESCRIPTION

Figure 1:
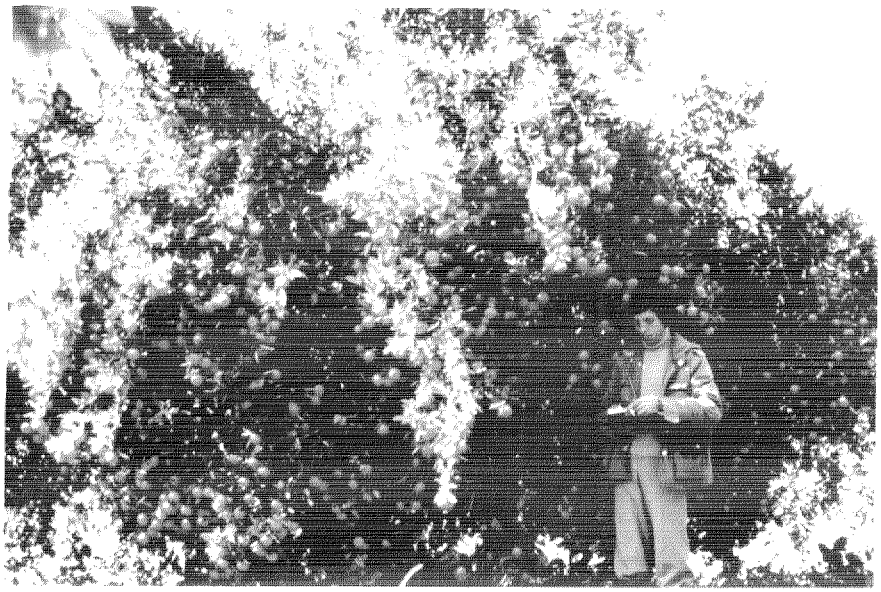
FIG. 1: The original tree at the Agricultural Experiment station — Afourer, Beni Mellal, 1983.
Figure 2:
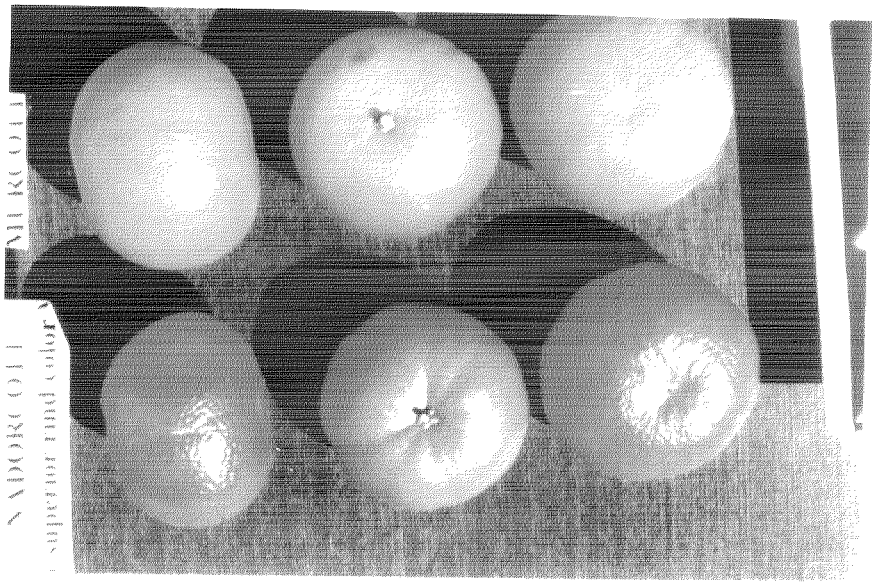
FIG. 2: Fruit of 'Nadorcott' compared to those of 'Murcott' — Beni Mellal 1992.
Figure 3:
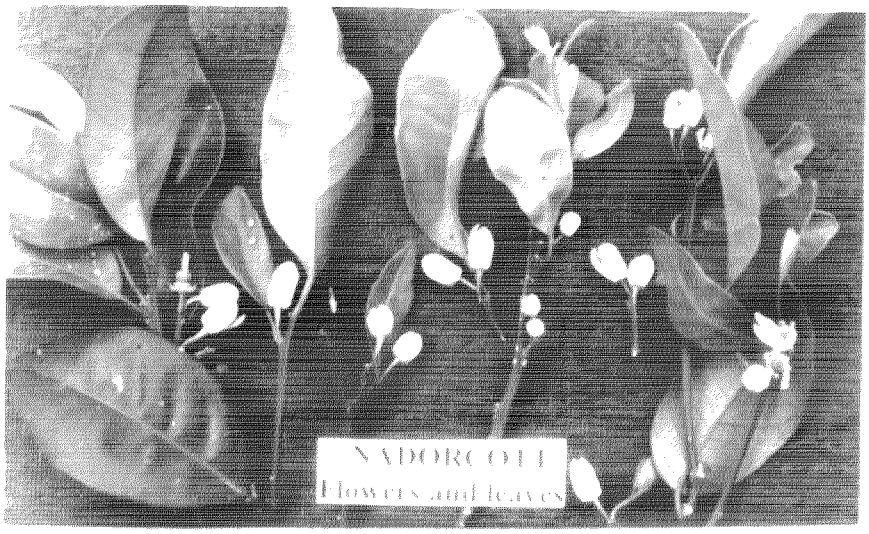
FIG. 3: Leaves and flowers of 'Nadorcott'.
Figure 4:
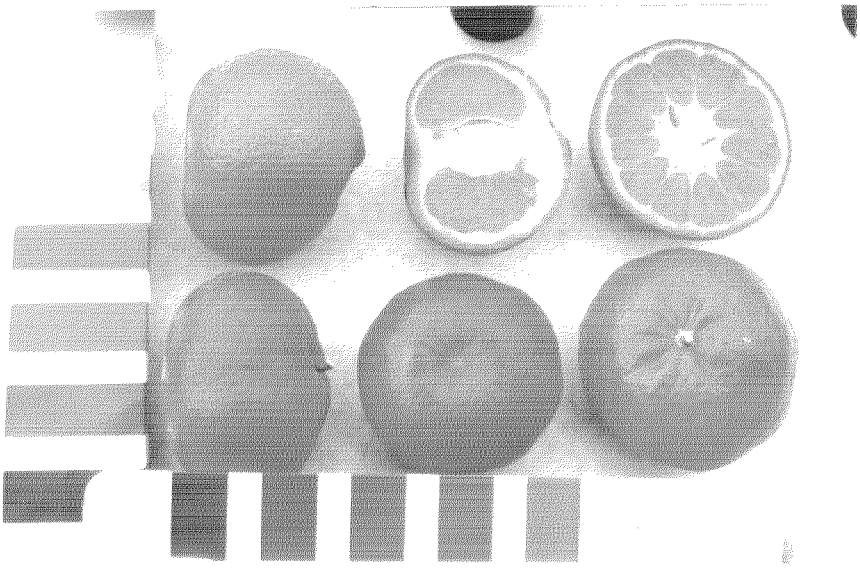
FIG. 4: Details of the 'Nadorcott' fruit: side, apex, base, cross and longitudinal section of 'Nadorcott' at Marrakech, December 1996.
Figure 5:
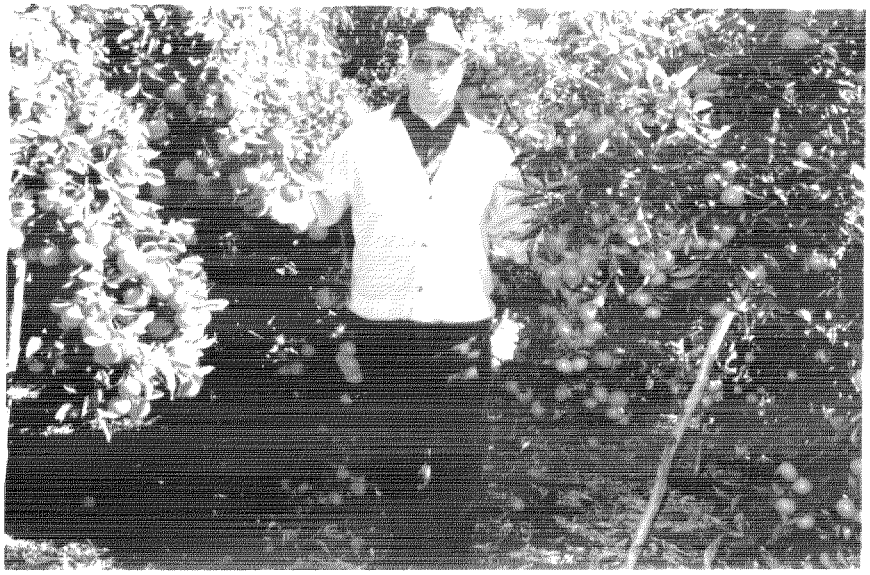
FIG. 5: Fructification of 'Nadorcott'.
Figure 6:
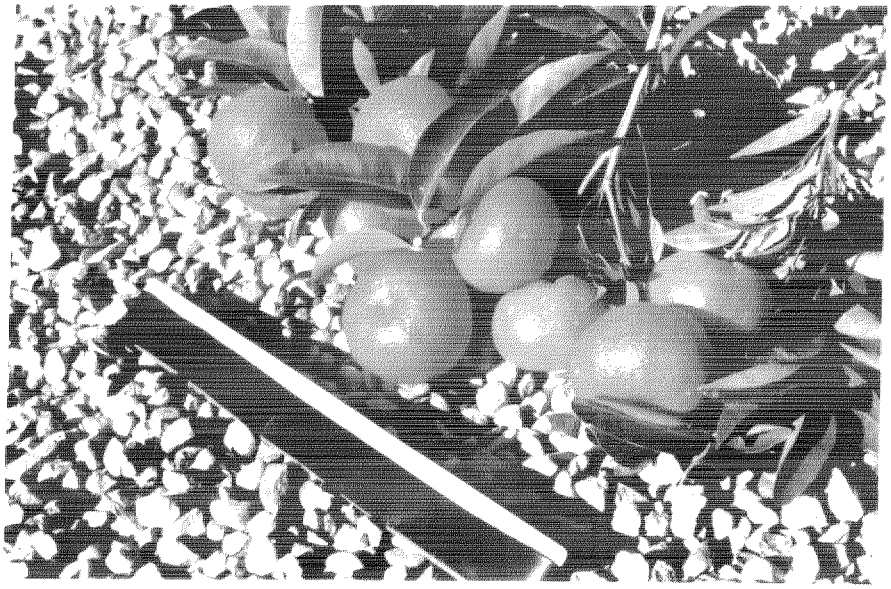
FIG. 6: Typical rind color — of 'Nadorcott' at Marrakech, in mid winter.
Figure 7:
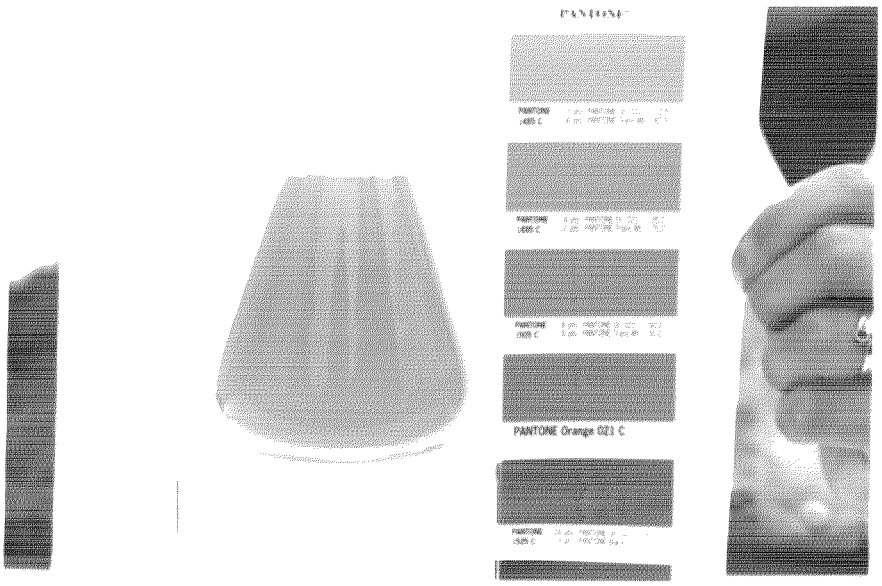
FIG. 7: Color of the juice of 'Nadorcott' at Marrakech, in mid winter.
Figure 8:
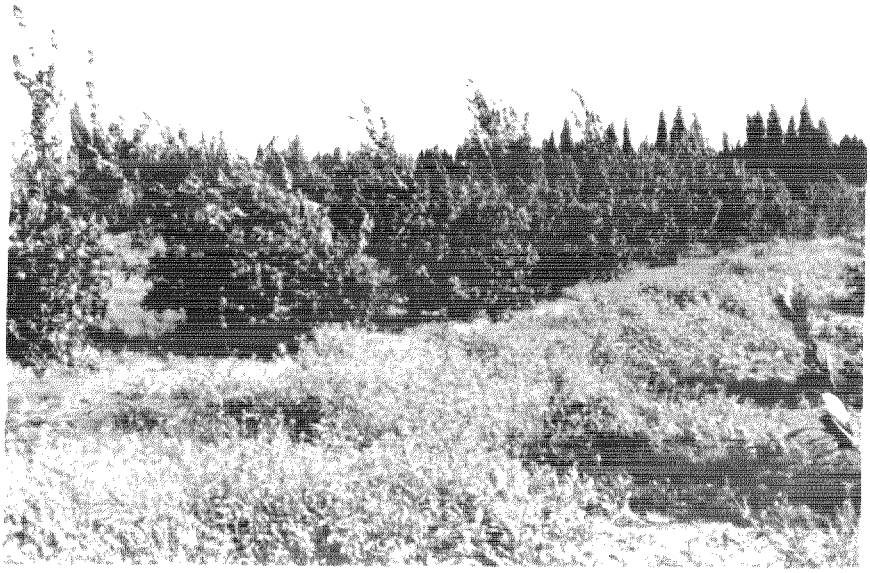
FIG. 8: Young orchard of 'Nadorcott', 2.5 years old at Marrakech, December 1996.
Figure 9:
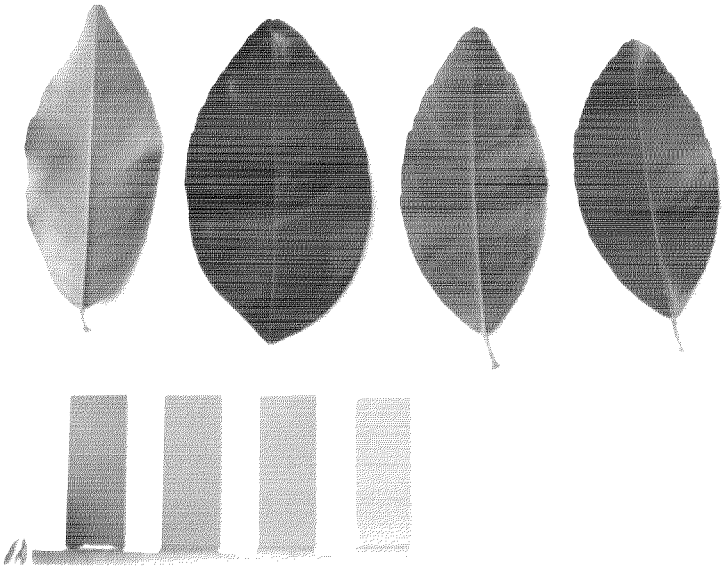
FIG. 9: The leaves of 'Nadorcott': upper and lower surfaces.

The following is a description of the 'Nadorcott' variety as observed under the growing conditions of Rabat, Beni Mellal and Marrakech. The colors except the color white referred to in the detailed description are according to the Pantone Color Formula Guide. Identification of the color white is according to the Colour Chart of The Royal Horticultural Society.

Tree: The tree is very vigorous, taller than most mandarin cultivars and its parent, the 'Murcott'. The young trees show an excellent rate of growth and vigor. The shape of the tree is upright in habit for young trees. When bearing frits, the vigorous shoots drop giving the canopy a spreading shape.

The older trees have a rounded shape with ascending shoots on the top of the canopy and dropped on the edge.

Foliage: The leaves look like those of 'Murcott' but less lanceolate, larger and not pointed. When ground, the leaves give an odor as that of willow leaf mandarin. The leaves are smooth on both sides.

*Size.*—Large for a mandarin group.

*Length.*—74 mm (with 10 mm for the petiole).

*Width.*—42 mm.

*Shape.*—Elliptic to oblong.

*Color.*—The upper surface is dark green (574C). The lower surface is lighter green (377U).

*Petiole.*—10 mm. Wings are absent.

*Marginal form.*—The margin is slightly serrated.

Flowers:

*Date of bloom.*—Occurs at the same time as other citrus cultivars: beginning of March for the region of Marrakech, February for Rabat.

*Number of petals.*—4 to 5.

*Number of sepals.*—4 to 5.

*Petal length.*—7 mm.

*Petal width.*—3.5 mm.

*Pedicel length.*—5 to 6 mm.

*Width of the closed flower.*—7 to 11 mm.

*Color of the petals.*—White (155C).

Fruit:

*Maturity.*—Mid-season (begins by mid-December). The fruits are harvested until the end of March.

*Size.*—Medium; the average fruit weight varies from 83 to 93 grams.

*Form.*—Oblate; both base and apex slightly depressed, the fruit shape is not perfectly round; the average diameter varies from 60 to 68 mm, the height of the fruit averages 46 to 49 mm. Those two parameters depend on the growing conditions. The ratio of diameter/height of the fruit is 1,24 to 1,38. The bigger fruits are short necked with prominent furrows.

Rind: The rind surface is smooth; orange red color (021U); this specific coloration is reached by the beginning of Janurary in Marrakech; the rind is thin: 2.5 to 3.5 mm with average of 2.8 mm; the adherence of the rind to the flesh is medium but the fruit is at least as easy to peel as the 'Clementine' fruit; finely pitted, medium number of oil glands: 50 per $cm^2$, oil glands globose and of medium size; the stylar scar is apparent and dry. It should be noted that the fruit on the sunny part of the tree might be rugose with a lighter orange color (137C); on the other hand, the shaded fruit has smooth rind with deep reddish orange color (1655C). In some cases, there is a pink color on the surface of contact between fruit. The fruit oil glands have refreshing effect and distinct and very pleasant smell. When over mature, the big fruit becomes puffy, but the flesh remains juicy.

Flesh; Irregular open axis, there are 8 to 13 segments per fruit with an average of 10; the segments are readily separated, the skin of the segment is tender. The pulp is uniform deep orange (151C); medium texture; vesicles globose to obovoid and medium to large.

Juice: Fruit is very juicy even before maturity: 50%. The juice has an orange color (1495U), a strong and attractive aroma and an excellent flavor. The total soluble solids rate (E) is high: 110 to 150 depending on the rootstock and the period of harvest, the acid content (A) is also high at the beginning of the maturity (11 to 14 grams per liter). The ratio E/A reaches 6.5 during December in the Marrakech area.

Seed content: Under self-pollination conditions, fruits are seedless (average 0.2 to 0.5 seed/fruit).

Tree storage: Fruits hang well on the tree even when over mature.

Use: Mainly fresh eating mandarin.

Keeping quality: Excellent.

Shipping quality: Excellent.

Resistance to diseases: No particular disorder noticed.

I claim:

1. A new and distinct variety of Mandarin Tangerine tree having the characteristics described and illustrated herein.

* * * * *